(12) United States Patent
Hatch

(10) Patent No.: US 6,645,180 B1
(45) Date of Patent: Nov. 11, 2003

(54) SINGLE-USE SYRINGE

(76) Inventor: Thomas Hatch, 757 Rosehurst Way, Lexington, KY (US) 40515

(*) Notice: Subject to any disclaimer, the term of this patent is extended or adjusted under 35 U.S.C. 154(b) by 98 days.

(21) Appl. No.: 09/663,294

(22) Filed: Sep. 15, 2000

(51) Int. Cl.[7] .......................... A61M 5/00; A61M 5/178
(52) U.S. Cl. ........................................ 604/181; 604/217
(58) Field of Search ................................. 604/181, 217

(56) References Cited

U.S. PATENT DOCUMENTS

| | | |
|---|---|---|
| 2,552,100 A | 5/1951 | Leonetti et al. |
| 3,114,369 A | 12/1963 | Hall |
| 3,736,933 A | 6/1973 | Szabo |
| 3,862,684 A | 1/1975 | Schmitt |
| 4,013,073 A | 3/1977 | Cunningham |
| 4,150,744 A | 4/1979 | Fennimore |
| 4,258,863 A | 3/1981 | Ness |
| 4,415,085 A | 11/1983 | Clarke et al. |
| 4,475,906 A | 10/1984 | Holzner |
| 4,548,601 A | 10/1985 | Lary |
| 4,573,977 A | 3/1986 | Crawford |
| 4,623,336 A | 11/1986 | Pedicano et al. |
| 4,921,137 A | 5/1990 | Heijenga |
| 4,955,871 A | 9/1990 | Thomas |
| 5,019,048 A | 5/1991 | Margolin |
| 5,195,985 A | 3/1993 | Hall |
| 5,261,881 A * | 11/1993 | Riner .................... 604/110 |
| 5,309,649 A | 5/1994 | Bergmann et al. |
| 5,417,659 A | 5/1995 | Gaba |
| 5,584,816 A | 12/1996 | Gyure et al. |
| 5,810,783 A | 9/1998 | Claro |
| 5,810,784 A | 9/1998 | Tamaro |
| 5,873,860 A | 2/1999 | Kahlert |
| 2001/0000471 A1 | 11/2001 | Yugari |

FOREIGN PATENT DOCUMENTS

| | | |
|---|---|---|
| FR | 1 385 377 A | 1/1965 |
| GB | 180 215 A | 5/1922 |

* cited by examiner

*Primary Examiner*—William C. Doerrler
*Assistant Examiner*—Filip Zec
(74) *Attorney, Agent, or Firm*—Pierce Atwood; Kevin M. Farrell

(57) ABSTRACT

Disclosed is a single-use syringe comprising a needle housing, a bore-containing fluid-delivery needle and a volume-containing element. The needle housing has a top surface to which the volume-containing element is attached, a needle attachment side to which the bore-containing needle is attached, and a fluid delivery channel in communication between the top surface and the needle attachment side. The volume-containing element is fluid-tight but for communication with the fluid-delivery and a filling port. Embodiments are disclosed which include vapor-permeable portions which facilitate lyophilization of materials in situ.

27 Claims, 5 Drawing Sheets

SINGLE-USE SYRINGE

BACKGROUND OF THE INVENTION

The storage and dispensing of fluids, and more particularly sterile fluids used in medical applications requiring use of a needle, is plagued by a host of difficulties which detract from the optimal use of such sterile fluids. For example, in cost-sensitive applications, multi-dose vials provide an economical means of packaging medical fluids but also increase the likelihood of contamination of the remaining contents when multiple needles are used to penetrate the sterile environment of the vial. This is an even greater problem in animal health applications where the same needle is often used to inject a medical fluid such as a vaccine into multiple animals. Re-entry of a contaminated needle into the multi-dose storage container may lead not only to a loss of sterility but to severe contamination of the remaining contents with infectious disease causing organisms. Such contamination may require the disposal of the remaining non-sterile medical fluid if not used immediately, or worse, the transmission of infectious disease organisms between animals.

When conventional syringes are used to draw fluids such as vaccines from multi-dose vials, considerable time and effort can be lost in the process, particularly in animal applications. The user must go to a cold storage area, locate a vial containing the desired fluid, transport the vial to the location where the fluid is to be administered, penetrate the sterile barrier of the vial with a needle, withdraw a single dose of fluid, and administer the dose to the animal. In many instances the vial is stored in a refrigerator at some distance from where the fluid is to be administered, particularly when the animal being treated is located in the field. After use, the vial containing the remaining fluid must be returned immediately to the refrigerator to maintain product quality. The time cost of maintaining cold chain conditions on the medical fluid can be a major inconvenience to the user and can result in variable observation of handling instructions on the product label. For the reasons discussed above, a cost-effective, preloaded, single-use syringe would represent a major advance in the art.

SUMMARY OF THE INVENTION

The present invention relates, in one aspect, to a single-use syringe comprising a needle housing, a bore-containing fluid-delivery needle and a volume-containing element. The needle housing has a top surface to which the volume-containing element is attached, a needle attachment side to which the bore-containing needle is attached, and a fluid delivery channel in communication between the top surface and the needle attachment side. The volume-containing element is fluid-tight but for communication with the fluid-delivery needle and a filling port. Embodiments are disclosed which include vapor-permeable portions which facilitate lyophilization of materials in situ.

DESCRIPTION OF PREFERRED EMBODIMENTS

The present invention relates to a disposable single-use syringe. The device finds application in a wide variety of medical, veterinary and commercial contexts. Generally speaking, embodiments of the present invention include a volume-containing element which is attached to one side of a needle housing. The volume-containing element communicates with a fluid-delivery needle via a fluid-delivery channel.

Figure 1:
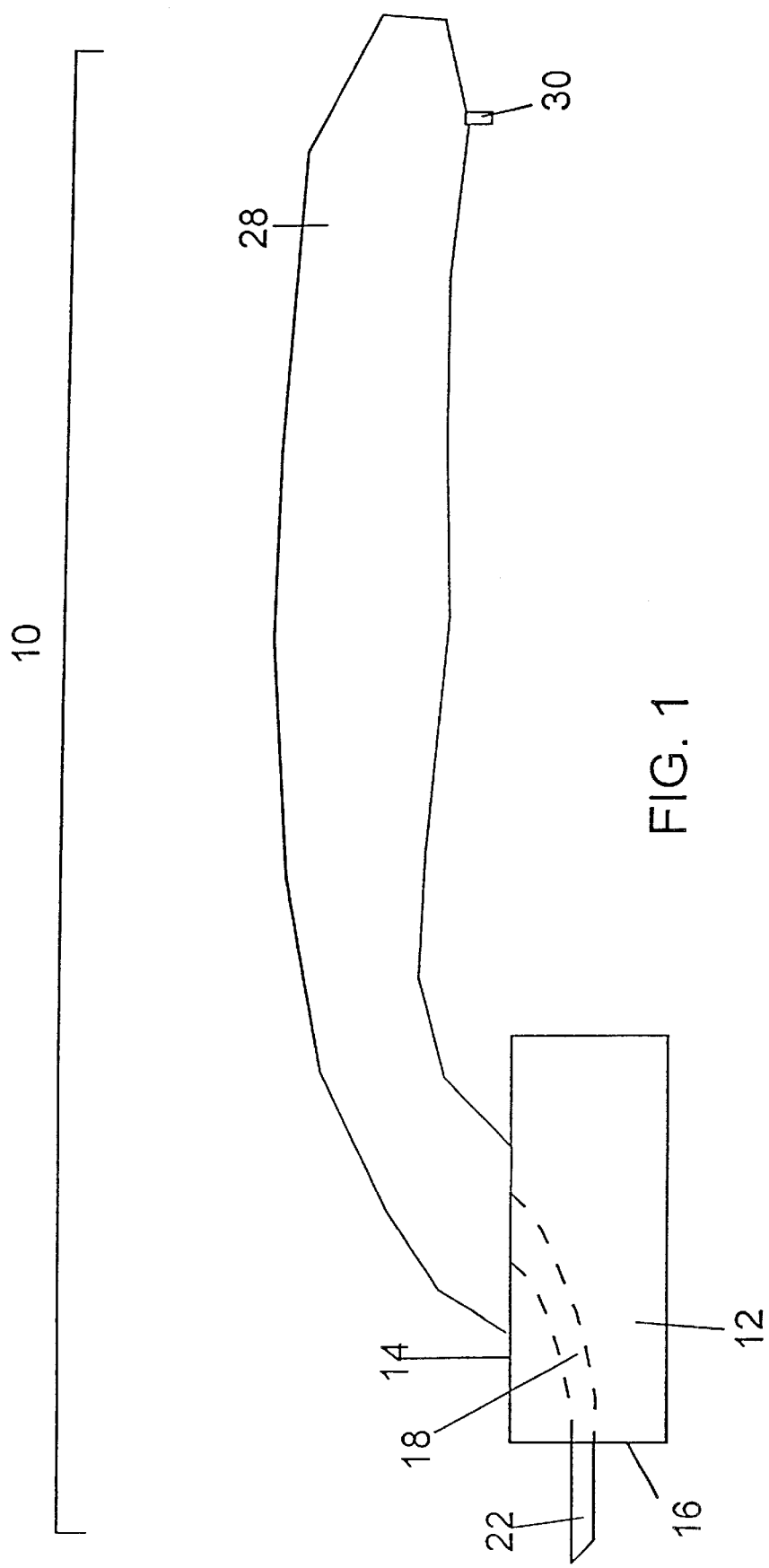
FIG. 1 is a side view of a single-use syringe of the present invention.

Referring to FIG. 1, a side view of the single-use syringe 10 of the present invention is shown. The device includes a needle housing 12. The needle housing 12 has a fluid-delivery channel 18 which communicates with a top surface 14 of the needle housing 12 via a fluid-delivery channel entrance (not visible) and the needle attachment side 16 of the needle housing via a fluid-delivery channel exit (not visible). A bore-containing fluid-delivery needle 22 is attached to the needle attachment side 16 and is in communication with the fluid-delivery channel 18. A volume-containing element 28 is attached to the top surface 14 of the needle housing 12. The volume-containing element 28 is fluid-tight but for communication with the fluid-delivery channel 18, and a filling port 30. A fluid tight seal (not shown) may be incorporated to prevent fluid from discharging through fluid-delivery needle 22 prior to use. A wide range of temporary, fluid tight seals for a bore-containing needle are known in the art and all are suitable for application in connection with the device of the present invention.

In preferred embodiments, the needle housing is produced from a plastic material. The production of the needle housing from a plastic material offers certain cost benefits when compared with other suitable alternatives (such as aluminum). In addition, the production of the needle housing from a plastic material offers the added benefit of enabling heat-sealing technologies to be used, for example, to attach the volume-containing element to the needle housing. Thus, in preferred embodiments, the volume-containing element 28 is also produced from a heat-sealable material. Thermoplastics (e.g., fluorocarbon and vinyl-chloride materials), foils or polyfoils are examples of materials useful for the production of the volume-containing element. As will be discussed more fully below, however, heat-sealing is but one method for the attachment of the volume-containing element 28 to the needle housing 12.

As mentioned above, the single-use syringe of the present invention can be used in a variety of applications, including medical or veterinary applications. For many such applications it is important that a sterile fluid be delivered using the device of the present invention. In many instances it will be desirable to sterilize the device of the present invention prior to the introduction of a sterile fluid into the volume-containing element. Sterilization in situ (i.e., after filling the single-use syringes) may be appropriate for some solutions. Preferably, however, the device of the present invention is sterilized prior to filling with a fluid. The sterilization of the device may be accomplished in any conventional manner. Methods for accomplishing this sterilization can include, without limitation, exposure to high temperature, irradiation and sterilizing fluids and gasses. The needle, needle channel and surfaces of the volume-containing element should be cleaned to remove pyrogens.

For medical and veterinary application in which the device of the present invention is to be used to inject a sterile fluid into a body, the fluid-delivery needle 22 is preferably a sterile steel hypodermic needle. For other applications in which the material in the fluid-containing element is not injected into a body, a plastic bore-containing needle of significantly larger internal bore may be appropriate. An example of such an application may be in the baking field in which the present device, outfitted with a blunt, large-bore plastic needle may be used for delivery of confectionery dyes.

The construction of the needle housing and the attachment of a needle to the needle housing are matters of routine experimentation to one skilled in the art. An example of a method for introducing the fluid-delivery channel into the needle housing would be to bore the channel from a housing blank using a drilling element or elements. Alternatively, a molded two-piece needle housing could be designed in which a portion of the fluid-delivery channel is molded into each half. When the halves are attached to one another (e.g., using an adhesive), the fluid-delivery channel is formed.

The two-piece needle housing embodiment can contain a shoulder or other retaining member near the exit of the fluid delivery channel into which a fluid-delivery needle can be inserted. When the two halves of the needle housing are attached to one another, the needle is held firmly in position. Other needle attachment fittings would be apparent, or designed through routine experimentation by one of skill in the art.

Figure 2:
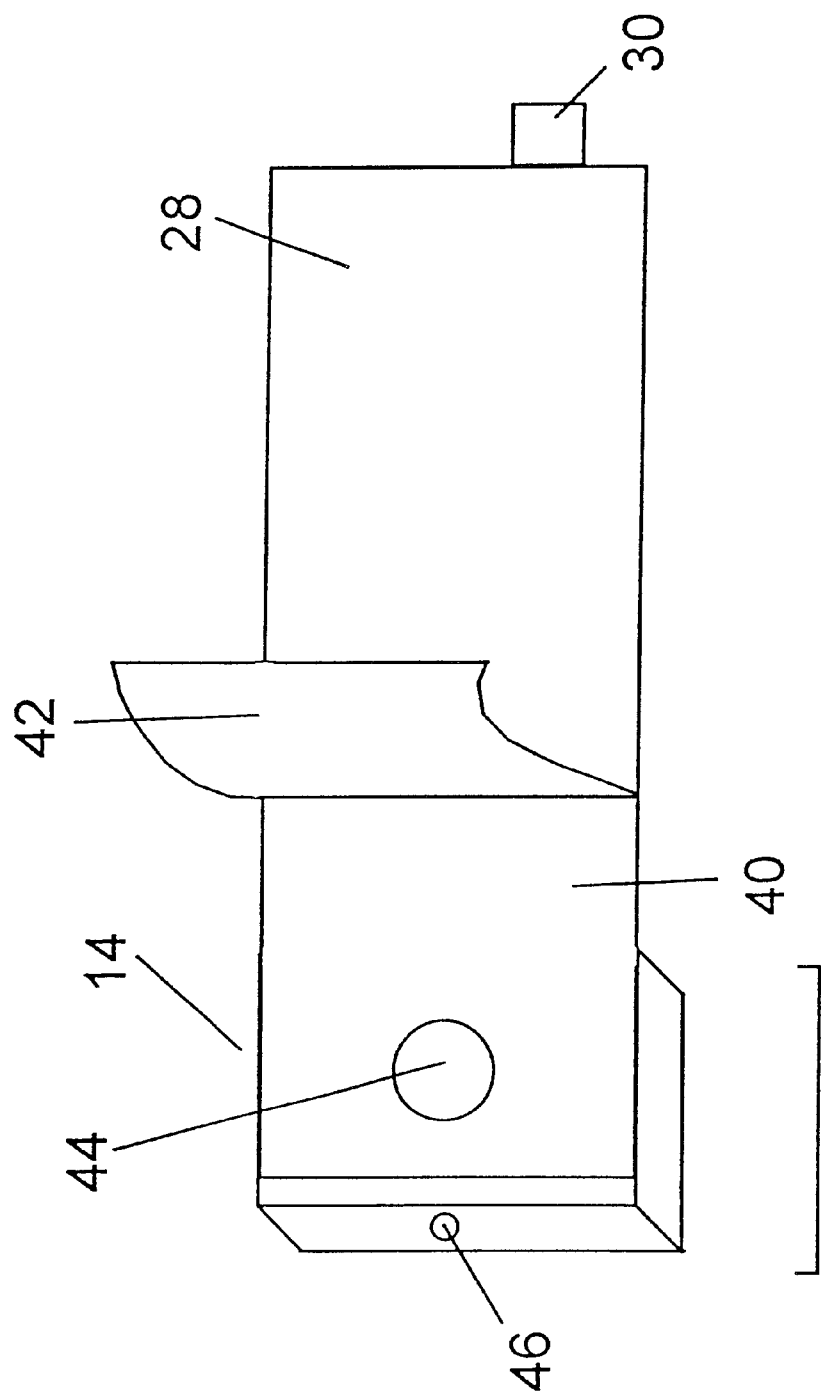
FIG. 2 is a perspective view of a single-use syringe of the present invention in which the volume-containing element is produced from two sheets of sealable material.

Referring to FIG. 2, the volume-containing element 28 may be produced by heat-sealing two sheets of heat-sealable material, directly or indirectly, to the top surface 14 of needle housing 12. In FIG. 2, the entrance to the fluid-delivery channel at the top surface 14 of the needle housing 12 is indicated by reference numeral 44. The exit of the fluid-delivery channel is indicated by reference numeral 46. In the embodiment of FIG. 2, a first sheet of heat-sealable material 40 is heat sealed to the top surface 14 of the needle housing 12. The heat seal between the top surface 14 of the needle housing 12 and the first sheet of heat-sealable material 40 is continuous in the area surrounding the top surface entrance 44 of the fluid-delivery channel. The portion of the first sheet of heat-sealable material 40 which covers the top surface entrance 44 to the fluid-delivery channel is sliced or removed to allow for the flow of fluid through the fluid-delivery channel. A second sheet of heat-sealable material 42 is then sealed to the first sheet of heat-sealable material 40 to form the volume-containing element 28. Thermoplastics, foils and polyfoils are examples of suitable heat-sealable materials for use in the construction of the volume-containing element. Those skilled in the art will be familiar with other materials suitable for this purpose.

The volume-containing element 28 is fluid tight but for liquid communication points at the fluid-delivery channel 18 and the filling port 30. The filling port 30 can be designed in a number of ways as will be apparent to one skilled in the art. For example, the filling port can be simply formed by leaving a small portion of the heat seal which forms the volume-containing element unsealed. A filling cannula can be inserted following construction of the device to add fluid. The fluid-filled volume-containing element is then sealed (e.g., by heat sealing) making the volume-containing element fluid tight but for communication with the fluid-delivery channel. A somewhat more complicated design which incorporates a continuous filling channel for filling a plurality of devices in sequence will be discussed below in connection with methods of manufacture. All disclosed embodiments are intended to be encompassed by Claim 1 as originally filed and the "filling port" limitation should be interpreted accordingly.

As an alternative to heat sealing, other attaching methods can be used to attach the volume-containing element to the needle housing. Such alternative techniques include, for example, adhesive bonding and ultrasonic welding. In one embodiment not shown here, the entrance 44 to the fluid-delivery channel (not shown) may be sealed by a rupturable seal. The rupturable seal is designed to rupture when pressure is applied to the volume-containing element 28.

Figure 3:
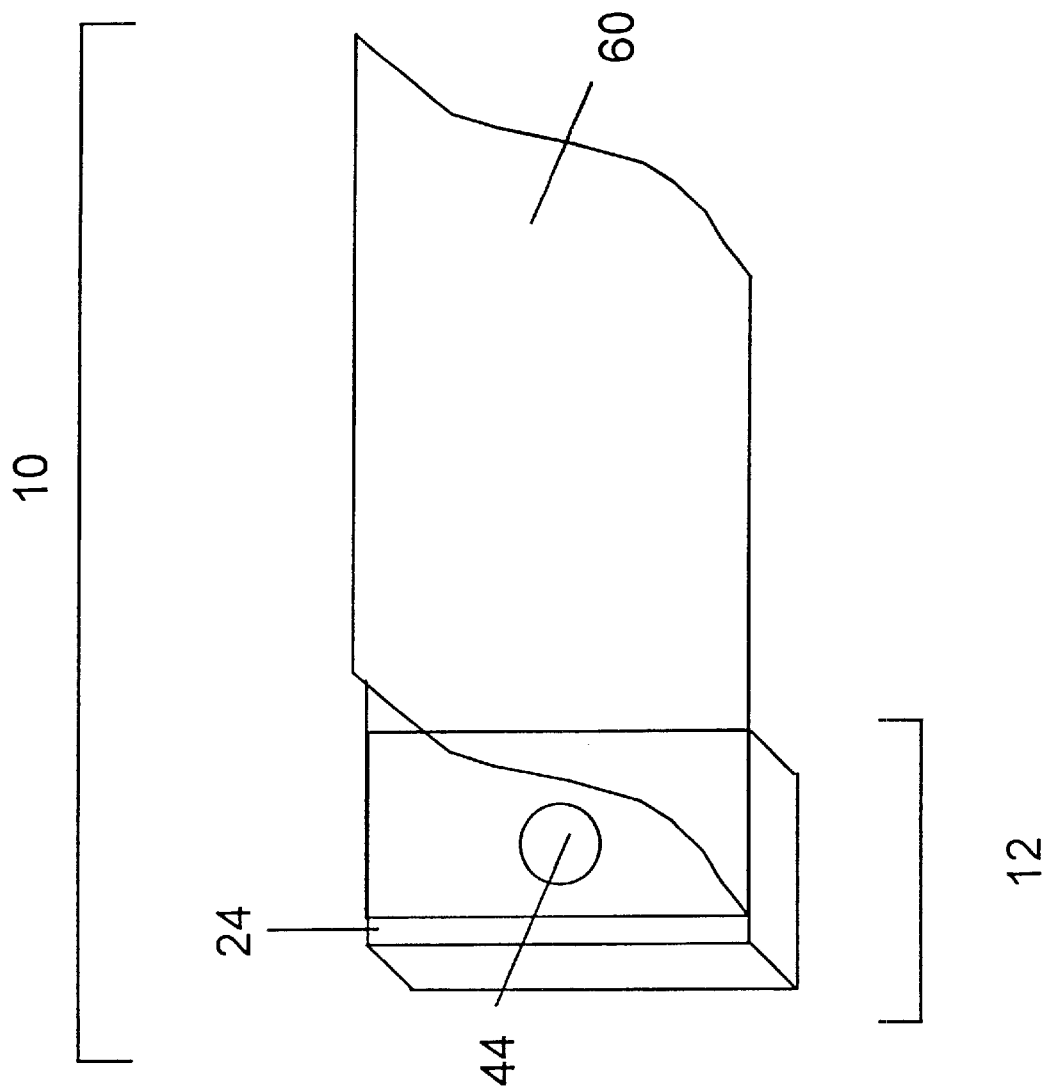
FIG. 3 is a perspective view of a singe-use syringe of the present invention in which the volume-containing element is produced from a single sheet of sealable material.

FIG. 3 shows an alternate embodiment for the single-use syringe 10. In this embodiment, the volume-containing element 28 is comprised of a single sheet of material 60 folded back upon itself. One skilled in the art will recognize that while FIG. 3 shows a sheet of material being folded from a first side edge, the sheet could also be folded from the top edge, the bottom edge or the second side edge. The sheet of material 60 is made out of any suitable material that is fluid tight and that can be sealed to itself and to the top surface 24 of the needle housing 12. In the preferred embodiment the sheet of material 60 is a heat-sealable material or a thermoplastic. One skilled in the art will recognize that the sheet of material 60 could also be a foil or polyfoil. The sheet of material 60 is sealed to itself and the top surface 24 of the needle housing 12 by any appropriate method including, for example, heat-sealing, adhesive bonding, or ultrasonic welding. Prior to completely sealing the sheet of material 60 to itself, the entrance 44 to the fluid-delivery channel (not shown) of the needle housing 12 must be unobstructed.

In a preferred method for manufacturing the single-use syringes of the present invention, a plurality of needle housings are provided. The plurality of needle housings are preferably connected along a side edge to form a continuous web. Perforations or partial cuts along the edges joining adjacent needle housings facilitate later separation. The continuous web of needle housings may be rolled to permit manufacturing to take place in a relatively small manufacturing area.

For example, a roll of needle housing blanks may be provided on a spool. An adjacent spool may contain a roll of heat-sealable plastic sheeting for use in the construction of the volume-containing element. The two rolls are then spooled out at substantially equal rates onto an assembly surface. On the assembly surface, heating elements are applied to seal the heat-sealable plastic sheeting to the plurality of needle housings. A blade can be included in the heating element which makes the seal around the entrance to the fluid-delivery channel such that the plastic is cut at the entrance at the same time that the sheet is being sealed to the needle housing. The sheet of heat-sealable material can then be folded onto itself and completely sealed along its perimeter where two unsealed edges meet.

In addition, in preferred embodiments, spaced-apart partial sealing lines are introduced at intervals along the web corresponding approximately to the width of the needle housing. These partial sealing lines form the individual volume-containing elements associated with each of the singe-use syringes. The seals are partial so that fluid communication is maintained along the web. With fluid communication throughout the web, a predetermined amount of fluid can be introduced into the web and directed to individual volume-containing elements. For example, the web may be filled with a fluid volume approximating one-half of the total volume of the web. The web is then sealed so that the fluid is sealed within the web. Beginning at one end of the sealed web, fluid is directed into an individual volume-containing element. The fluid communication to this now filled individual volume-containing element is then sealed (e.g., by heat sealing). This process is then repeated along the web until all of the volume-containing elements are filled and sealed.

Alternatively, a filling cannula can be inserted into the web to fill each volume-containing element in series. As each individual volume-containing element is filled, the filling cannula is advanced and the filled volume-containing element is sealed thereby interrupting fluid communication with the now filled volume-containing element. U.S. Pat. No. 3,941,306 (the disclosure of which is incorporated herein by reference) discloses a system of interconnected sealed and unsealed bags. Such a system could be adapted for use in connection with the present invention thereby enabling the individual single-use syringes to be filled from a moving filling cannula, rather than having to fill each syringe individually through an external filling port.

Figure 5:
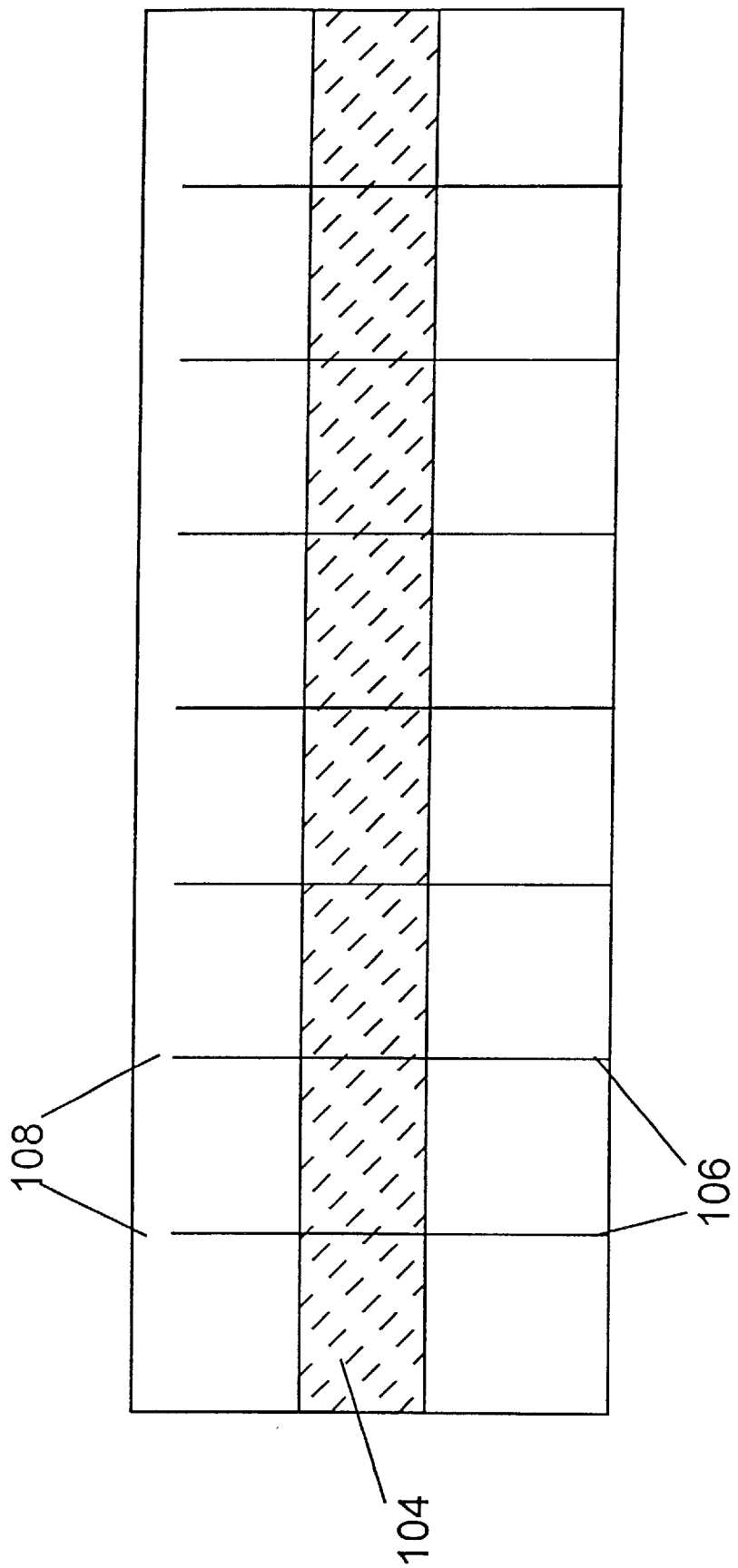
FIG. 5 is a top view of an unfilled web for use in the production of individual fluid-containing elements adapted for lyophilization.

Referring to FIG. 5, the present invention also relates to a web of individual fluid-containing elements adapted for lyophilization. The embodiment depicted in FIG. 5 is produced from a fluid-tight sealable tube having a vapor-permeable portion 104. Preferably the sealable tube is produced from a heat-sealable material of the type described above in connection with other embodiments of the invention. It is not required, however, that the tube be heat-sealable.

FIG. 5 shows a top view of this embodiment in an unfilled state. The vapor-permeable portion 104, extends along the full length of the web. Individual volume-containing elements are formed by the introduction of partial transverse seals 106 along the web. The transverse seals 106 are partial, thereby forming a fluid-communication channel 108 along one edge of the web.

A tube having a vapor-permeable portion for use in the construction of the embodiment shown in FIG. 5 can be produced in a variety of ways. In a preferred embodiment, the tube is produced from a foil or polyfoil sheet. For example, a sheet of material which is 10 inches wide and 300 feet long may be provided. To introduce a vapor-permeable portion into the sheet, a continuous longitudinal portion of the sheet is appropriately treated. For example, the continuous longitudinal portion can be exposed to gamma radiation and then treated with acid. This treatment will render the continuous longitudinal portion vapor-permeable. The continuous longitudinal portion must, as a percentage of total surface area of the web, be significant enough to allow vapor to be withdrawn from fluid-containing volumes within a reasonable period of time. For example, the vapor-permeable portion can comprise at least about 5% to about 10% of the total surface area of the web.

Following the introduction of the vapor-permeable portion, the polyfoil sheet is folded upon itself and sealed to form a tube. Transverse partial seals are subsequently introduced to generate the embodiment as depicted in FIG. 5.

As an alternative to the method of introducing the vapor-permeable portion described above, it is also possible to attach, in an overlapping manner, a vapor-permeable material to a vapor (and fluid) impermeable material. Vapor-permeable membranes are, generally speaking, hydrophobic membranes which contain pores large enough for water vapor to pass through, but too small for microorganisms to penetrate. Such pores preferably have a size of less than about 0.5 um, and most preferably less than about 0.2 um. For use in connection with the present invention it is desirable to select a vapor-permeable membrane which maintains strength and is tear-resistant when wet.

Examples of useful materials for construction of the vapor-permeable portions include foils, semi-permeable papers of cellulose and cellulose derivatives such as cellulose acetates. Membranes of films of polymer compounds (e.g., polytetrafluoroethylene or polypropylene) can also be used. Commercially available vapor-permeable membranes, including Goretex, are also useful in connection with the present invention. Generally speaking, any suitably strong film membrane which is impermeable to microorganisms, but vapor-permeable, is useful.

As discussed above in connection with the polyfoil example, the vapor-permeable material is sealed to a material which is vapor and fluid impermeable. Another second seal is then introduced longitudinally to form a tube containing a vapor-permeable portion. Partial transverse seals are then introduced to form the embodiment depicted in FIG. 5.

In another embodiment, a fluid containing a material to be lyophilized is introduced into the tube. Preferably the tube is filled to approximately half of its volume. A series of new seals are introduced thereby forming individual volume-containing elements. The newly introduced seals are substantially parallel to the end seal.

Upon completion of the seal introduction, completing the formation of the web of sealed volume-containing elements, the web is in condition for lyophilization. Lyophilization (sometimes referred to as freeze-drying) is a well known process (see, e.g., Ullmanns Enzkyklopadie der Technischen Chemie, 3rd edition, Vol. I, p. 556 et seq.). For example, in freeze-drying pharmaceutical preparations in ampules, the procedure typically is to provide the bottles containing the material to be lyophilized fitted with a bacterial filter. The material to be lyophilized is frozen, and then dried in the ampules in a first drying step to such an extent that the sublimation of the frozen solvent is concluded. Subsequently, in a second drying stage (the post-drying or residual-drying stage) the remaining moisture is removed from the material.

U.S. Pat. No. 5,309,649 discloses a process and container for freeze-drying under sterile conditions. More specifically, the cited U.S. patent discloses a container for the freeze-drying of a material in bulk. The process and container incorporate a vapor-permeable membrane. The present invention incorporates a similar vapor-permeable membrane, but is directed toward the production of smaller amounts, for example, less than about 5 gram quantities of lyophilized material in each volume-containing element in the context of a large scale run.

In modern lyophilization equipment, cooling and heating means are commonly provided to accelerate the freeze-drying process. To facilitate the lyophilization of the disclosed web of individual fluid-containing elements adapted for lyophilization, a lyophilization chamber may be fitted with a spiral cooling/heating element. The web of individual fluid-containing elements is wrapped around the spiral cooling/heating element in such a way that the vapor-permeable portion is not in direct contact with the spiral cooling/heating element.

Upon completion of the lyophilization process, the vapor-permeable portion of the resulting web of individual lyophilized material-containing elements must be sealed under anhydrous conditions. The sealing of the vapor permeable portion under anhydrous conditions ensures that the lyophilized material will maintain the very dry and stable state created through the lyophilization process. The vapor-permeable region can be sealed using any suitable process. Suitable processes include, for example, the application of a spray sealant compound or tape sealant. Once sealed, the individual lyophilized material-containing elements may be separated from one another and packaged for distribution individually or in bulk.

In another aspect, the present invention relates to a single-use syringe and methods of production which incorporate a vapor-permeable membrane in the volume-containing element discussed previously. All aspects of the production of this embodiment are identical to that described for the non-vapor-permeable single-use syringe embodiments, but for the presence of the vapor-permeable region in the volume-containing element. Following lyophilization and sealing of the vapor-permeable region, the freeze-dried material contained in such a single-use syringe could be rehydrated with a diluent either through the needle, or through a provided filling port in the volume-containing element.

Figure 4:
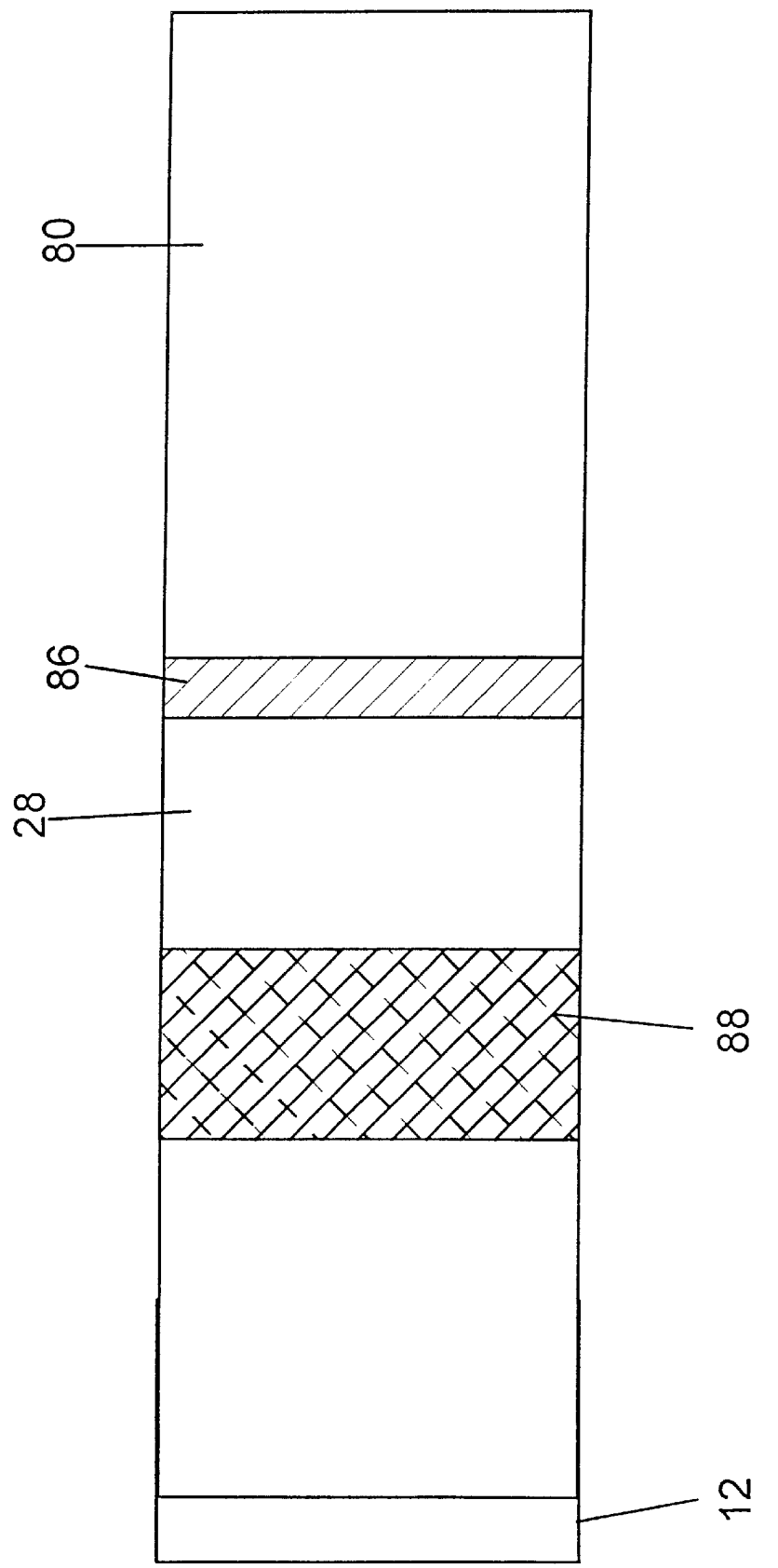
FIG. 4 is a top view of a single-use syringe of the present invention which is comprised of a first and a second volume-containing element, the first volume-containing element having a vapor-permeable region.

In another embodiment which is represented in FIG. 4, a second volume-containing element 80 is provided together with the first volume-containing element 28, the first volume-containing element 28 being provided with a vapor permeable region 88. The first volume-containing element is attached to needle housing 12 as discussed in connection with other embodiments of the present invention. The second volume-containing element is not provided with a vapor-permeable region and it is filled with the desired diluent for rehydration of the lyophilized material. A rupturable, fluid-tight seal 86 is provided between the first volume-containing element 28 and the second volume-containing element 80. Following lyophilization and sealing of the vapor-permeable region in the first volume-containing element 28, the lyophilized material is rehydrated with diluent by applying sufficient pressure to the second volume-containing element 80 to rupture the rupturable seal or burstable seam 86. Rupturable seals or burstable seams are well known in the art. An example of such a burstable seam is disclosed in U.S. Pat. Nos. 3,736,933, 4,475,906, and 5,706,937, the disclosures of which is incorporated herein by reference.

What is claimed is:

1. A single-use syringe comprising:
   a) a solid needle housing, said needle housing comprising:
      i) a top surface;
      ii) a needle attachment side; and
      iii) a fluid-delivery channel in communication between the top surface and the needle attachment side;
   b) a bore containing fluid-delivery needle attached to the needle attachment side of the needle housing, the bore of the fluid-delivery needle communicating with the fluid-delivery channel; and
   c) a volume-containing element attached to the top surface of the needle housing, the two-sided volume-containing element being fluid tight but for communication with the fluid-delivery channel and a filling port.

2. The singe-use syringe of claim 1 where the volume-containing element, needle, and the interior of the needle housing are sterilized.

3. The single-use syringe of claim 2 where the sterilization is accomplished by a method selected from the group consisting of exposure to high temperature, irradiation, and sterilizing fluid or gas.

4. The single-use syringe of claim 1 wherein the volume-containing element is attached by:
   a) providing a first sheet of material and sealing the first sheet of material to the top surface of each needle housing in the area surrounding the fluid-delivery channel;
   b) removing or relieving any obstruction from the fluid-delivery channel at the top surface of the needle housing; and
   c) providing a second sheet of material and sealing the second sheet to the first sheet to form the volume-containing element.

5. The single-use syringe of claim 4 where the first sheet and second sheet are produced from a heat-sealable material.

6. The single-use syringe of claim 5 where the first sheet and second sheet are produced from a thermoplastic, foil or polyfoil material.

7. The single-use syringe of claim 4 where a rupturable obturator is placed over the opening in the fluid-delivery channel on the top surface of the needle housing.

8. The single-use syringe of claim 4 where the first sheet and second sheet of material air attached directly or indirectly to the housing, said attachment being accomplished by a method selected from the group consisting of heat sealing, adhesive bonding, and ultrasonic welding.

9. The single-use syringe of claim 1 wherein the volume-containing element is attached by:
   a) providing a sheet of material and sealing the sheet of material to the top surface of each needle housing in the area surrounding the fluid-delivery channel;
   b) removing or relieving any obstruction from the fluid-delivery channel at the top surface of the needle housing; and
   c) folding the sheet of material onto itself and sealing the sheet of material to itself to form the volume-containing element.

10. The single-use syringe of claim 9 where the sheet of material is a heat-sealable material.

11. The single-use syringe of claim 10 where the heat-sealable material is a thermoplastic, foil or polyfoil material.

12. The single-use syringe of claim 9 wherein a rupturable seal interrupts communication between the volume-containing element and the fluid-delivery channel.

13. The single-use syringe of claim 9 where the sheet of material is attached directly or indirectly to the top surface of the housing, said attachment being accomplished by a method selected from the group consisting of heat sealing, adhesive bonding, and ultrasonic welding.

14. A method for producing a single-use syringe, comprising:
   a) providing a plurality of solid needle housings, each needle housing comprising:
      i) a top surface;
      ii) a needle attachment side; and
      iii) a fluid-delivery channel in communication between the top surface and the needle attachment side;
   b) a temporarily sealed bore-containing fluid-delivery needle attached to the needle attachment side of the needle housing, the bore of the fluid-delivery needle communicating with the fluid-delivery channel; and
   c) attaching to the top surface of each needle housing a two-sided volume-containing element, the two-sided volume-containing element being fluid tight but for communication with the fluid-delivery channel and a filling port.

15. The method of claim 14 where the volume-containing element, needle, and the interior of the needle housing are sterilized.

16. The method of claim 14 where the sterilization is accomplished by a method selected from the group consisting of exposure to high temperature, irradiation, and sterilizing fluid or gas.

17. The method of claim 14 wherein the volume-containing element is attached by:
   a) providing a first sheet of material and sealing the first sheet of material to the top surface of each needle housing in the area surrounding the fluid-delivery channel;
   b) removing or relieving any obstruction from the fluid-delivery channel at the top surface of the needle housing; and
   c) providing a second sheet of material and sealing the second sheet to the first sheet to form the volume-containing element.

18. The method of claim 17 where the first and second sheets are produced from a heat-sealable material.

19. The method of claim 18 where the heat-sealable material is a thermoplastic, foil or polyfoil material.

20. The method of claim 17 where a rupturable obturator is placed over the opening in the fluid-delivery channel on the top surface of the needle housing.

21. The method of claim 11 where the first sheet and second sheet of material are attached directly or indirectly to the housings, said attachment being accomplished by a method selected from the group consisting of heat sealing, adhesive bonding, and ultrasonic welding.

22. The method of claim 14 wherein the volume-containing element is attached by:
   a) providing a sheet of material and sealing the sheet of material to the top surface of each needle housing in the area surrounding the fluid-delivery channel;
   b) removing or relieving any obstruction from the fluid-delivery channel at the top surface of the needle housing; and
   c) folding the sheet of material onto itself and sealing the sheet of material to itself to form the volume-containing element.

23. The method of claim 22 where the sheet of material is a heat-sealable material.

24. The method of claim 23 where the heat-sealable material is a thermoplastic, foil or polyfoil material.

25. The method of claim 22 where a rupturable obturator is placed over the opening in the fluid-delivery channel on the top surface of the needle housing.

26. The method of claim 22 where the sheet of material is attached directly or indirectly to the top surface of the housings, said attachment being accomplished by a method selected from the group consisting of heat sealing, adhesive bonding, and ultrasonic welding.

27. The single-use syringe of claim 1 wherein a portion of the volume-containing element is produced from a vapor-permeable material.

* * * * *

UNITED STATES PATENT AND TRADEMARK OFFICE
CERTIFICATE OF CORRECTION

PATENT NO. : 6,645,180 B1
DATED : November 11, 2003
INVENTOR(S) : Thomas Hatch

It is certified that error appears in the above-identified patent and that said Letters Patent is hereby corrected as shown below:

Column 7,
Line 56, delete "bore containing" and substitute therefore -- bore-containing --.

Column 8,
Line 26, delete "air" and substitute therefore -- are --.

Column 9,
Line 30, delete "11" and substitute therefore -- 17 --.

Signed and Sealed this

Second Day of March, 2004

JON W. DUDAS
*Acting Director of the United States Patent and Trademark Office*